United States Patent [19]

Tachibana

[11] Patent Number: 4,723,045
[45] Date of Patent: Feb. 2, 1988

[54] PROCESSES FOR PREPARING CHOLESTA-1,5,7-TRIEN-3-OL

[75] Inventor: Yoji Tachibana, Kawagoe, Japan

[73] Assignees: Nisshin Flour Milling Co., Ltd.; Nisshin Chemicals Co., Ltd., both of Japan

[21] Appl. No.: 8,828

[22] Filed: Jan. 30, 1987

[30] Foreign Application Priority Data

Feb. 5, 1986 [JP] Japan .................................. 61-22185

[51] Int. Cl.$^4$ ............................................ C07C 35/42
[52] U.S. Cl. .................................................... 568/714
[58] Field of Search ........................................ 568/714

[56] References Cited

PUBLICATIONS

Turner et al., "J. Chem. Soc". (1969) p. 2568.
Romo et al., "J. Org. Che.", (1950) vol. 15, p. 896.
Woodward et al., "J. Amer. Chem. Soc.", vol. 74, No. 17 pp. 4223+ (1952).
Kaneko et al., "Tetrahedron" vol. 30, p. 2701 (1974).
Guest et al., "J. Chem. Soc. " Parkin I (1979) p. 1695.

Primary Examiner—Werren B. Lone
Attorney, Agent, or Firm—Abelman Frayne Rezac & Schwab

[57] ABSTRACT

New processes for preparing cholesta-1,5,7-trien-3-ol which is a key intermediate in the synthesis of 1α-hydroxyvitamin D$_3$. The processes utilize the steps of reacting cholesta-1,4,6-trien-3-one with isopropenyl acetate in the presence of an acid catalyst followed by reduction of the resultant cholesta-1,3,5,7-tetraen-3-yl-acetate.

8 Claims, No Drawings

PROCESSES FOR PREPARING CHOLESTA-1,5,7-TRIEN-3-OL

FIELD OF THE INVENTION

This invention relates to processes for preparing cholesta-1,5,7-trien-3-ol which is a key intermediate in the synthesis of 1α-hydroxyvitamin $D_3$.

BACKGROUND OF THE INVENTION

Previously, cholesta-1,5,7-trien-3-ol has been prepared by the base-catalyzed rearrangement of cholesta1,4,6-trien-3-one to isomerize the 4,6-diene to the 5,7-diene, followed by the reduction of the formed cholesta-1,5,7-trien-3-one (C. Kaneko et al., Tetrahedron, 30, 2701, 1974 and D. W. Guest et al., J Chem. Soc., Perkin I, 1979, 1695). In that case, however, the yield of cholesta-1,5,7-trien-3-ol is about 25 to about 40%. Thus, there was such a drawback that so far as the final product, 1α-hydroxyvitamin $D_3$ is synthesized via the steps of the prior arts as referred to above, the yield of the final product will considerably be low and moreover, much time and labor are required for the purification and isolation of the desired product.

Under such circumstances, it has been ardently desired to prepare cholesta-1,5,7-trien-3-ol, the intermediate for the synthesis of 1α-hydroxyvitamin $D_3$, in more favorable yields by an economical and efficient way.

SUMMARY OF THE INVENTION

An essence of the present invention is the discovery that cholesta-1,4,6-trien-3-one which can be readily prepared from cholesterol is reacted with isopropenyl acetate in the presence of an acid catalyst to provide cholesta-1,3,5,7-tetraen-3-yl-acetate in high yields, and this acetate compound is converted quantitatively to the desired compound of the invention, cholesta1,5,7-trien-3-ol in good yields.

Cholesta-1,4,6-trien-3-one used as the starting material in the invention is readily prepared from inexpensive cholesterol and hence the process of the present invention is of industrial as well as economical advantage.

DETAILED DESCRIPTION OF THE INVENTION

More particularly, the invention provides a process for preparing cholesta-1,5,7-trien-3-ol of the formula

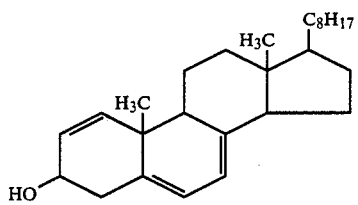

which comprises reacting cholesta-1,4,6-trien-3-one of the formula

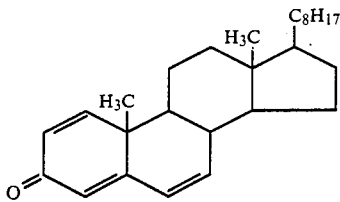

with isopropenyl acetate of the formula

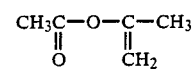

in the presence of an acid catalyst to provide cholesta-1,3,5,7-tetraen-3-yl-acetate of the formula

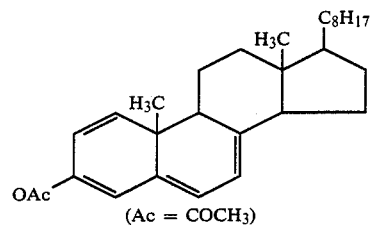

(Ac = $COCH_3$)

and reducing the cholesta-1,3,5,7-tetraen-3-yl-acetate.

Cholesta-1,4,6-trien-3-one (I) used as the starting material in the practice of the invention may be prepared by the oxidation of cholesterol, for example, with DDQ (2,3-dichloro-5,6-dicyano-p-benzoquinone) or the like (A. B. Turner et al., J. Chem. Soc., (C), 1968, 2568 or J. Romo et al., J. Org. Chem., 15, 896, 1950). Furthermore, the compound (I) may also be synthesized by the dehydrogenation of cholesta-4,6-dien-3-one with DDQ (Proc. Chem. Soc., 1960, 14).

Acid catalysts used in the practice of the invention include organic acids such as paratoluenesulfonic acid, methanesulfonic acid and the like, and inorganic acids such as hydrochloric acid, sulfuric acid, acid potassium sulphate and the like. The acid catalyst is used in the range of 0.1 to 10 moles per mole of the starting material (I).

Isopropenyl acetate (II) is used in the range of 1 to 100 moles and preferably 10 to 50 moles per mole of cholesta-1,4,6-tiren-3-one (I).

In practicing the process of the invention, the reaction between the compounds (I) and (II) may be carried out in the presence of an organic solvent commonly used in chemical reactions, such as butyl acetate, toluene and the like. Though the reaction temperature employed is not particularly limited, the reaction between the above-mentioned two compounds smoothly proceeds at a reflux temperature of the solvent used.

The reaction product (compound III) of the compound (I) and the compound (II) is neutralized and dried to a concentrate which is subjected to reduction reaction. Examples of reducing agents used in the reduction of the compound (II) include metal hydrides such as lithium aluminumhydride ($LiAlH_4$), sodium borohydride ($NaBH_4$), calcium borohydride ($Ca(BH_4)_2$), zinc borohydride ($Zn(BH_4)_2$) and the like. Of these metal hydrides, preferred is $Ca(BH_4)_2$. The reduction is carried out in an organic solvent such as ether. The reaction temperature is in the range of from −30° C. to room temperature and preferably from −5° C. to 5° C.

The desired compound of the invention can be prepared, after completion of the reduction, by distilling off the solvent from the reaction mixture and crystallizing the residue.

According to the process of the invention as described hereinabove, the desired compound, cholesta1,5,7-trien-3-ol (IV) is prepared in good yield of more than 50%, starting from cholesta-1,4,6-trien-3-one (I). Thus, the process of the present invention can achieve a pronounced improvement in the yield of the desired compound over the aforesaid prior art processes.

To further illustrate this invention, and not by way of limitation, the following examples are given.

EXAMPLE 1

To a mixture of 38 g (0.1 mol) of cholesta-1,4,6-trien-3-one and 17 g (0.1 mol) of paratoluenesulfonic acid were added 400 g (4 mol) of isopropenyl acetate, and the mixture was heated under reflux for 3 hours. The reaction solution was thoroughly washed with water until it was neutral, and dried over sodium sulfate A solution of the thus obtained concentrate in 600 ml of ether was added dropwise at a temperature of −5° C. to −10° C. to a reducer solution and stirred at 0° C. for 6 hours, said reducer solution being prepared by cooling a solution of 90 g of calcium chloride in 1,500 ml of methanol to a temperature of −5° C. to −10° C., then adding dropwise thereto a solution of 45 g of sodium borohydride in 2,000 ml of ethanol, and stirring the reaction solution at a temperature of −5° C. to −10° C. for 60 minutes. After completion of the reaction, 50% acetic acid was added to the reaction mixture and the resultant solution was extracted with ether. The ethereal layer separated was washed with water and then sodium bicarbonate solution, dried over sodium sulfate and distilled under reduced pressure to remove ether therefrom. The residue was recrystallized from acetone to yield 23.9 g of cholesta-1,5,7-trien-3-ol (IV), m.p. 126°–127° C. The yield was 63%.

EXAMPLE 2

To a mixture of 38 g (0.1 mol) of cholesta-1,4,6-trien-3-one (I) and 34 g (0.2 mol) of paratoluenesulfonic acid were added 200 ml of butyl acetate and further 200 g (2 mol) of isopropenyl acetate, and the resulting mixture was heated under reflux for 5 hours. After completion of the reaction, the same treatment as in Example 1 was carried out to yield 25.2 g of cholesta-1,5,7-trien-3-ol (IV). The yield was 66%.

EXAMPLE 3

To a mixture of 19 g (0.05 mol) of cholesta-1,4,6-trien-3-one (I), 4.8 g (0.05 mol) of methanesulfonic acid and 200 g (2 mol) of isopropenyl acetate were added 200 ml of toluene, and the resulting mixture was then heated under reflux for 6 hours. After completion of the reaction, the same treatment as in Example 1 was carried out to yield 11.7 g of cholesta-1,5,7-trien-3-ol (IV). The yield was 61%.

EXAMPLE 4

To a mixture of 19 g (0.05 mol) of cholesta-1,4,6-trien-3-one (I), 6.8 g (0.05 mol) of potassium acid sulphate and 200 g (2 mol) of isopropenyl acetate were added 200 ml of butyl acetate, and the resulting mixture was heated under reflux for 7 hours. After completion of the reaction, the same treatment as in Example 1 was carried out to yield 11.1 g of cholesta-1,5,7-trien-3-ol (IV). The yield was 58%.

What is claimed is:

1. A process for preparing cholesta-1,5,7-trien-3-ol which comprises reacting cholesta-1,4,6-trien-3-one with isopropenyl acetate in the presence of an acid catalyst selected from the group consisting of paratoluene sulfonic acid, methanesulfonic acid, hydrochloric acid, sulfuric acid and acid potassium sulphate to form cholesta-1,3,5,7-tetraen-3-yl acetate, and reducing the same with metal hydrides at temperatures in the range of from −30 degrees Centigrade to room temperature.

2. The process of claim 1 wherein the acid catalyst is paratoluenesulfonic acid, methanesulfonic acid or potassium acid sulphate.

3. The process of claim 1 wherein the acid catalyst is used in the range of from 0.1 to 10 moles per mole of cholesta-1,4,6-trien-3-one.

4. The process of claim 1 wherein isopropenyl acetate is used in the range of from 10 to 50 moles per mole of cholesta-1,4,6-trien-3-one.

5. The process of claim 1 wherein cholesta-1,4,6-trien-3-one is reacted with the isopropenyl acetate in an organic solvent.

6. The process of claim 5 wherein the organic solvent is butyl acetate.

7. The process of claim 1 wherein the reduction is carried out at a temperature of from −5° C. to 5° C. in an organic solvent.

8. The process of claim 7 wherein the organic solvent is ether.

* * * * *